United States Patent
Battung et al.

(10) Patent No.: US 8,486,445 B2
(45) Date of Patent: Jul. 16, 2013

(54) SELF-MICROEMULSIFYING MITOTANE COMPOSITION

(76) Inventors: Florian Battung, Paris (FR); Emad Hassan, Hunt Valley, MA (US); Lionel Sansoe, Brussels (BE)

(*) Notice: Subject to any disclaimer, the term of this patent is extended or adjusted under 35 U.S.C. 154(b) by 0 days.

(21) Appl. No.: 13/322,222

(22) PCT Filed: May 24, 2010

(86) PCT No.: PCT/IB2010/052292
§ 371 (c)(1),
(2), (4) Date: Jul. 9, 2012

(87) PCT Pub. No.: WO2010/136952
PCT Pub. Date: Dec. 2, 2010

(65) Prior Publication Data
US 2013/0017258 A1    Jan. 17, 2013

(30) Foreign Application Priority Data
May 25, 2009 (EP) .................................. 09160999

(51) Int. Cl.
*A61K 9/107* (2006.01)
*A61K 9/113* (2006.01)
*A61K 9/48* (2006.01)
*A61K 31/02* (2006.01)

(52) U.S. Cl.
USPC ....................................................... 424/456

(58) Field of Classification Search
USPC .................. 424/400–456, 751, 758; 514/750, 514/748
See application file for complete search history.

(56) References Cited

U.S. PATENT DOCUMENTS 4,146,648 A    3/1979 Yabut
6,451,339 B2 *  9/2002 Patel et al. ..................... 424/451

OTHER PUBLICATIONS

Attivi, D. et al. "Formulation Et Pharmacocinetique De Systemes Autoemulsionnats De Mitotane (O,P'-ODD)" XP002545683, Jun. 15, 2008, retrieved from the Internet: http://www.snphpu.com/infos.asp?InNum=ln00001562&ThNum=Th0000005.
Trotta, M. et al. "Emulsions containing partially water-miscible solvents for the preparation of drug nanosuspensions" *Journal of Controlled Release*, 2001, pp. 119-128, vol. 76.
Written Opinion in International Application No. PCT/IB2010/052292, Nov. 23, 2011, pp. 1-5.

* cited by examiner

*Primary Examiner* — Frederick Krass
*Assistant Examiner* — Thuy Le
(74) *Attorney, Agent, or Firm* — Saliwanchik, Lloyd & Eisenschenk

(57) ABSTRACT

The invention relates to a self-microemulsifying drug delivery system ("SMEDDS") of mitotane, with enhanced bioavailability. More particularly the invention provides a mitotane oily formulation comprising propylene glycol monocaprylate (10 to 30% w/w), propylene glycol dicaprate (20 to 60% w/w) and polyoxyethylenesorbitanne monooleate (10 to 30% w/w).

15 Claims, 1 Drawing Sheet

SELF-MICROEMULSIFYING MITOTANE COMPOSITION

CROSS-REFERENCE TO RELATED APPLICATION

This application is the U.S. national stage application of International Patent Application No. PCT/IB2010/052290, filed May 24, 2010, the disclosure of which is hereby incorporated by reference in its entirety, including all figures, tables and amino acid or nucleic acid sequences.

The invention relates to a self-microemulsifying drug delivery system ("SMEDDS") of mitotane, with enhanced bioavailability.

TECHNICAL BACKGROUND

Mitotane (o,p'-DDD or 1,1-dichlorodiphenyldichloroethane) is an adrenolytic agent which is particularly useful in the treatment of non-resectable and metastasized adrenocortical carcinoma.

However mitotane has poor solubility in gastro-intestinal tract and low bioavailability when administered as a conventional tablet in humans. Attempts were made to solve this problem. A first self-microemulsifying drug delivery system ("SMEDDS") of mitotane was developed, comprising mitotane dissolved in a matrix composed of an equal mixture of Capryol®90, Tween®20 and Cremophor EL® (33:33:33) (Attivi et al, "Development of a self-microemulsifying drug delivery system of mitotane (o,p'-DDD) using a mixture design methodology", Chimiometrie 2006, Ajana Imane, 2006, Master "Sciences de la vie et de la santé", Nancy-Université). However this system could not load more than 250 mg of mitotane in 1000 mg of matrix, which is not enough to produce capsules of an acceptable size and would therefore seriously entail patients' compliance with the treatment. Optimization of this system was thus needed.

SUMMARY OF THE INVENTION

The invention provides a delivery system which incorporates high mitotane loads without forming precipitates in the presence of water.

More particularly, the invention provides a mitotane oily formulation which comprises mitotane in a matrix comprising a. propylene glycol monocaprylate; from 10 to 30% of the total weight of the mitotane oily formulation (w/w)
b. propylene glycol dicaprate; from 20 to 60% of the total weight of the mitotane oily formulation (w/w)
c. polyoxyethylenesorbitanne monooleate. from 10 to 30% of the total weight of the mitotane oily formulation (w/w)

Advantageously, this matrix can accommodate a drug loading of at least 33%, preferably at least 39%.

This oily formulation is capable of forming a microemulsion in situ with the biological fluids of the body.

The invention further provides a pharmaceutical composition comprising such mitotane oily formulation.

This pharmaceutical composition, which is preferably in the form of a capsule, is useful in treating cancer, in particular adrenocortical carcinoma.

Another subject of the invention is a method for preparing a mitotane oily formulation suitable for forming a self-microemulsifying drug delivery system, which method comprises dissolving mitotane in a mixture of propylene glycol monocaprylate, propylene glycol dicaprate and polyoxyethylenesorbitanne monooleate in proportions as recited above.

DETAILED DESCRIPTION

Definitions:

The term 'matrix' refers to a mixture of excipients.

The term 'mitotane oily formulation' refers to a matrix in which mitotane has been incorporated.

Drug loading corresponds to the weight of mitotane with respect to the total weight of the matrix. (Equation (1))

$$\text{Drug Loading} = \frac{\text{weight of mitotane}}{\text{weight of matrix}} \times 100 \quad \text{Equation (1)}$$

SMEDDS (self-microemulsifying drug delivery systems) are defined as isotropic mixtures of lipid, surfactant, cosurfactant, and drug that rapidly form a microemulsion when mixed with water. Such systems are described in greater details in Grove and Müllertz, "Liquid Self-Microemulsifying Drug Delivery Systems", Oral Lipid-Based Formulations—Enhancing the Bioavailability of Poorly Water-Soluble Drugs, edited by David J. Hauss, Informa Healthcare, 2007, Chapter 5. Self-emulsifying formulations are readily dispersed in the gastro-intestinal tract, where the motility of the stomach and small intestine provides the agitation necessary for emulsification.

In the present mitotane formulation, the lipophilic phase comprises propylene glycol dicaprate, polyoxyethylenesorbitanne monooleate that acts as a surfactant, and propylene glycol monocaprylate that acts as a cosurfactant.

Propylene glycol monocaprylate is available under the name Capryol®90 (Gattefossé).

Propylene glycol dicaprate is available under the name Captex®100 (Abitec corp.). Polyoxyethylenesorbitanne monooleate is available under the name Tween®80 (Sigma) or is also known as polysorbate 80 (or "PS 80" in the examples below).

In a particular embodiment, the oily formulation has a drug loading of at least 33%, preferably between 33% and 67%, and more preferably between 37% and 54%.

The mitotane oily formulation comprises a. from 10 to 30% w/w of propylene glycol monocaprylate, preferably from 15 to 20%, more preferably from 15 to 17% w/w;

b. from 20 to 60% w/w of propylene glycol dicaprate, preferably from 35 to 50%, more preferably from 38 to 42% w/w;

c. from 10 to 30% w/w of polyoxyethylenesorbitanne monooleate, preferably from 15 to 20%, more preferably from 15 to 17% w/w.

The mitotane oily formulation of the invention makes it possible to load at least 33%, preferably at least 39% of mitotane (i.e. 400 mg mitotane for 1000 mg of the matrix made of the mixture of lipid, surfactant and cosurfactant).

In a preferred embodiment, propylene glycol monocaprylate, propylene glycol dicaprate and polyoxyethylenesorbitanne monooleate represent a total amount of between 65 and 75% w/w in the mitotane oily formulation.

The oily formulation of the invention advantageously forms a microemulsion comprising droplets having a size of less than 200 nm, when mixed with water or HCl.

The mitotane oily formulation can be packaged in any pharmaceutical composition for oral administration.

Suitable oral compositions that comprise the oily formulation of the invention are generally capsules, including hard gelatin capsules or soft gelatin capsules. For instance, soft gelatin capsules are made with a gelatin shell, optionally in association with plasticizers such as glycerine and/or sorbitol. Encapsulation is achieved by techniques known in the art.

In another embodiment, the composition may be a liquid dispersed directly into the patient's mouth.

The pharmaceutical composition may then comprise water or an aqueous phase, in which the oily mitotane formulation is dispersed in the form of a microemulsion.

In a further embodiment, the mitotane oily formulation may be packaged into a solid dosage form, in a state readily converted to a microemulsion in vivo, which thereby enhances the dissolution of the drug.

The composition of mitotane oily formulation for therapeutic use advantageously contains between 100 and 400 mg mitotane, preferably between 100 and 300 mg.

A particular example of a composition according to the invention is a soft gelatin capsule encapsulating an oily formulation comprising from 33% to 66% of mitotane drug load and a matrix comprising:

a. propylene glycol monocaprylate: from 15 to 17% of the total weight of the mitotane oily formulation (w/w)
b. propylene glycol dicaprate: from 38 to 42% of the total weight of the mitotane oily formulation (w/w)
c. polyoxyethylenesorbitanne monooleate: from 15 to 17% of the total weight of the mitotane oily formulation (w/w)

The mitotane oily formulation of the invention, which is suitable for forming a self-microemulsifying drug delivery system may be prepared by dissolving mitotane in a mixture of propylene glycol monocaprylate, propylene glycol dicaprate and polyoxyethylenesorbitanne monooleate in proportions as recited above.

Drug loading of at least 33%, preferably at least 39%, can be achieved by immediate dispersion upon dilution into a homogenous solution.

If desired, the dissolution step may also be carried out by mixing for at least 5 minutes with heating to not more than 40-50° C.

The SMEDDS system of the invention enhances the dissolution of mitotane, and its bioavailability. Further food effect is reduced.

The examples and figures illustrate the invention without limiting its scope.

LEGENDS TO THE FIGURES

EXAMPLES

Example 1

Screening of Mitotane SMEDDS Formulations

Figure 1:
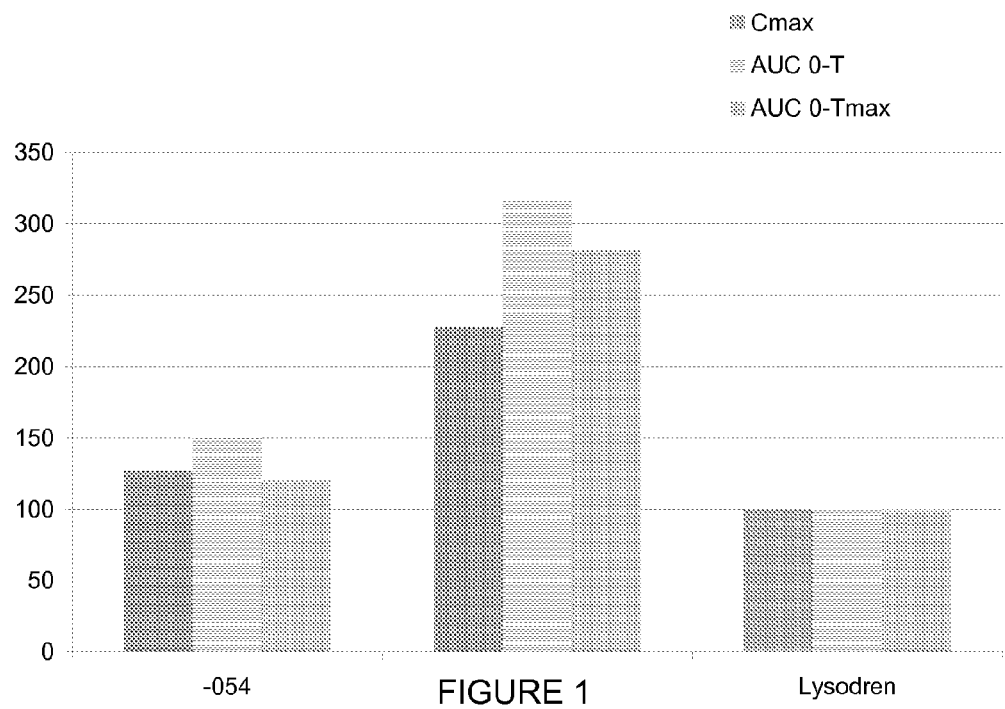
FIG. 1 is a graph that shows relative bioavailability vs lysodren (LYSO=Lysodren. Absorption of Lysodren is set as 100%).

Various SMEDDS formulations were screened for drug solubility, stability, and water tolerance.

Solubility was determined by incremental loading of mitotane.

A typical increment solubility study is summarized below:

One gram of vehicle was weighed into a 5 mL glass vial. Mitotane was added in increments of 10 to 20 mg. The contents were mixed. If mitotane dissolved (yielding a clear solution) another increment of mitotane was added. If mitotane did not dissolve, the contents were mixed for at least 5 minutes with heating to not more than 45° C.±5° C. Clarity of the solution was visually determined after each addition. Clear drug solutions were stored at room temperature for 24 hours and were then re-evaluated for clarity. The increments of mitotane added that produced a clear solution were summed, and this solubility was reported. A visual description of the material after the addition of the final increment was also noted. Due to the drug precipitation overnight in some samples, selected systems were tested at 50% and 55% drug loading in a direct loading solubility study.

A direct loading solubility study is summarized below:

One gram of vehicle was weighed into a 5 mL glass vial. The full amount of Mitotane was added in a single portion. The contents were heated to 45° C.±5° C. and mixed for at least two hours; during this time clarity was assessed every thirty minutes. Drug solutions were then stored at room temperature for 24 or 48 hours and were re-evaluated for clarity.

Stability was determined by placing the systems in a refrigerator (5° C.) or left at room temperature. At a minimum of 24 hours, solutions were visually evaluated. Any precipitate was noted.

Since water migration often occurs during manufacturing of soft gelatin capsules, a water uptake study was performed to evaluate the stability of mitotane solutions during the encapsulation and drying processes. Mitotane oily formulation and matrix were tested. The water uptake study was performed as follows:

3.0 g of mitotane oily formulation (with 50% drug loading) was weighed into a scintillation vial;
300 mg of water (10% w/w of mitotane oily formulation) was weighed and placed in the vial and then vortex mixed for a minimum of 5 minutes;
clarity of solution was visually determined;
if the solution was clear, an additional 300 mg of water was added (to bring the total added water to 20% w/w) then vortex mixed for a minimum of 5 minutes;
clarity of mixture was visually determined.

Microemulsions comprising droplets of a size inferior to 200 nm appear as clear solutions. Any hazy appearance or precipitate is noted.

Water tolerance study further allows to determine whether the system will self-emulsify in the presence of gastro-intestinal fluid in vivo, for instance.

Table 1 shows formulations with the best drug loading, which were selected for further studies.

Prior art formulation from Attivi et al, 2006, supra, is included in Table 1, for comparison purposes.

Formulations numbered 1 to 4 were eventually set aside, as high mitotane loads could not be incorporated.

TABLE 1

Comparative formulations

| Batch | Matrix (excipients ratio) | Drug loading |
|---|---|---|
| Attivi et al, 2006 | Capryol90:Tween20:Cremophor EL (1:1:1 w/w) | ≦25% |
| Comparative Test # 1 | Capryol90:Captex100:Labrasol (1:1:1 w/w) | 25% |
| Comparative Test # 2 | Capryol90:Captex100:Labrasol (56:22:22 w/w) | 25% |
| Comparative Test # 3 | Triethyl citrate:Captex100:Labrasol (1:1:1 w/w) | 25% |
| Comparative Test # 4 | Triethyl citrate:Captex100:Labrasol (56:22:22 w/w) | 25% |
| Formulation of the invention (Batch # 054) | Capryol90:Captex100:PS80 (1:1:1 w/w) | about 40% |
| Formulation of the invention (Batch # 057) | Capryol90:Captex100:PS80 (22:56:22 w/w) | about 40% |

Table 2 shows the characteristics of the two selected formulations.

TABLE 2

Selected formulations

| Batch # | Drug loading Mitotane (%) | Matrix excipient ratio | | | Diameter (nm) |
|---|---|---|---|---|---|
| | | Capryol 90 | Captex 100 | PS 80 | |
| -054 | About 40 | 1 | 1 | 1 | 93.68 (water) 81.03 (HCl) |
| -057 | About 40 | 22 | 56 | 22 | 125.84 (water) 138.68 (HCl) |

Example 2

Bioavailability and Absorption Studies

Formulations #054 and 057 according to the invention (see Example 1) were tested in dogs, in a screening study vs. Lysodren® (mitotane tablets commercially available from HRA pharma).

Three Beagle dogs/group were used per formulation. One group is administered with one Lysodren tablet comprising 500 mg of mitotane, one group is administered with two hard gelatin capsules comprising 280 mg mitotane each in formulation #054 and one group is administered with two hard gelatin capsules comprising 280 mg mitotane each in formulation #057.

The formulations were compared in fed and fasted conditions, including administrations on fed dogs and then fasted dogs in cross over with a wash out period of 3 weeks. 10 samples were collected at: 0, 1, 2, 3, 4, 5, 6, 8, 10 and 12 hours post administration.

Relative bioavailability data vs Lysodren® are as follows:
Lysodren®: 100%
Batch #054: 150
Batch #057: 317%
See FIG. 1.

Figure 2:
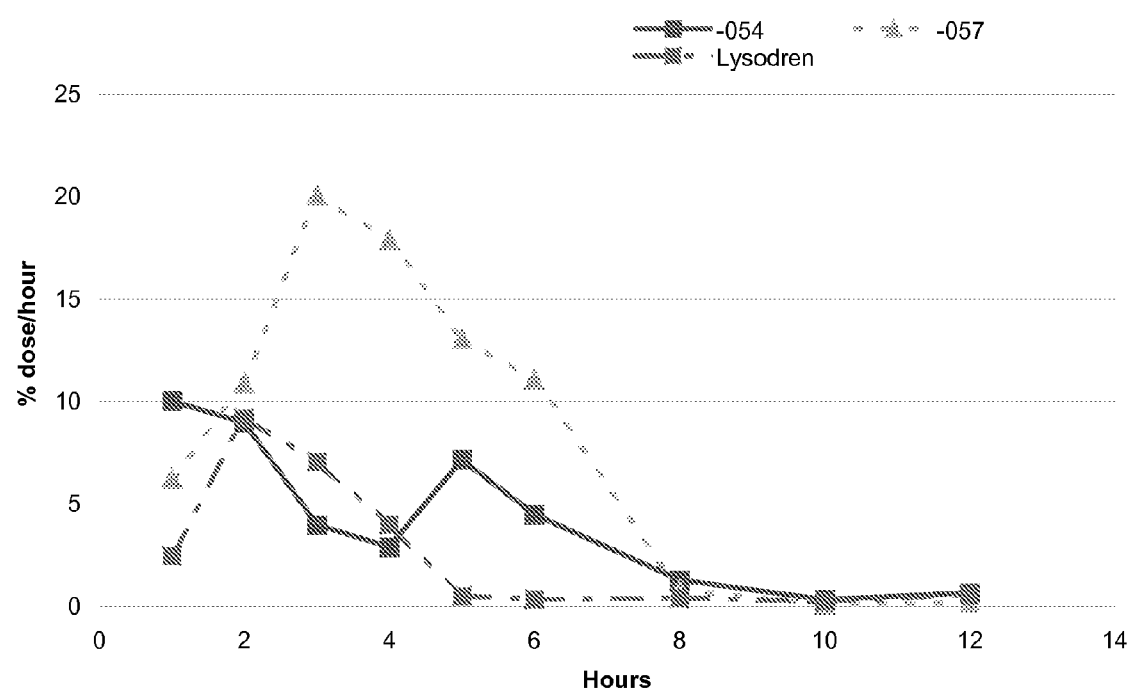
FIG. 2 is a graph that shows mitotane rate of absorption in fed conditions.

Absorption is slower for the two formulations of the invention (about 8 hours) than for Lysodren® (about 5 hours), which might be explained by an increase of lymphatic absorption. Such slow absorption (vs a mesenteric absorption) is advantageous in that it reduces the variations of absorption which are inherent to the use of mitotane. See FIG. 2.

Food effect on mitotane absorption is dramatically reduced with the two formulations of the invention (Lysodren® is substantially not absorbed at all without food).

TABLE 3

Food effect

| Formulation | Cmax Fed/Cmax Fasted | AUCt Fed/AUCt Fasted |
|---|---|---|
| Batch # 054 | 4 | 7 |
| Batch # 057 | 32 | 95 |

Example 3

Manufacturing of Mitotane SMEDDS Soft Gelatin Capsules

This example provides a protocol for manufacturing mitotane SMEDDS soft gelatin capsules having the following composition:

TABLE 4A

Quantitative formula for gel mass (Gel mass Batch size: 250 kg):

| Ingredient(s) | % w/w |
|---|---|
| Gelatin USP/NF (150Bloom Limed Bone, Type B) | 42.00 |
| Glycerin, USP 99.7% | 3.00 |
| Sorbitol Special | 18.00 |
| Purified water, USP | 34.92 |
| Opatint White (G-18000) | 2.00 |
| FD&C Blue # 1 | 0.08 |
| TOTAL | 100.0 |

TABLE 4B

Quantitative formula for capsule fill:

| Ingredient(s) | Mg/capsule | % weight of ingredient/weight of total mitotane oily formulation |
|---|---|---|
| Mitotane | 250.00 | 28.5 |
| Capryol 90 | 138.1 | 15.75 |
| Captex 100 | 350.8 | 40.00 |
| Polysorbate 80 | 138.1 | 15.75 |
| TOTAL | 877.0 | 100.0 |

Brief Manufacturing Procedure:
Fill Material:
  1. Charge the Capryol 90 into a container equipped with an overhead mixer.
  2. Mix to create a vortex 3. Charge Captex 100 into the mixing Capryol 90. Mix until homogenous solution is obtained.
4. Charge Polysorbate 80, mix until a homogenous solution is obtained.
5. Heat to 45° C.±5° C.
6. Once the temperature is in the above mentioned range, slowly charge the mitotane into the mixing solution. Mix until mitotane is completely dissolved into solution.
7. Deaerate final solution.

Gelatin Mass:
1. Reserve approximately 1 liter of water. Charge remaining purified water, USP, into gelatin melter and adjust the temperature to 90° C.
2. Charge sorbitol special and glycerine, USP 99.7%.
3. Charge Gelatin and heat to 80° C. under continuous mixing until gelatin granules are completely dissolved.
4. In a separate pot, charge colorants. Mix until a homogeneous suspension is obtained.
5. Charge step 4 into step 3 under continuous mixing.
6. Rinse step 5 container with the reserved purified water and charge into step 3. Mix until a homogenous gel mass is obtained.
7. Deaerate the gel mass (air vacuum adjusted to 25-30 in Hg).

Encapsulation and Processing:
1. Carry out the encapsulation
2. Tumble-dry the capsules
3. Tunnel-dry the capsules

The invention claimed is:

1. A mitotane oily formulation comprising mitotane in a matrix comprising:
   a) from 10 to 30% w/w of propylene glycol monocaprylate;
   b) from 20 to 60% w/w of propylene glycol dicaprate; and
   c) from 10 to 30% w/w of polyoxyethylene sorbitan monooleate.

2. The oily formulation of claim 1, comprising a drug load of mitotane of at least 33%.

3. The oily formulation of claim 1, comprising a drug load of mitotane of at least 39%.

4. The oily formulation of claim 2, comprising a drug load of mitotane of between 33% and 66%.

5. The oily formulation of claim 4, comprising a drug load of mitotane of between 37% and 54%.

6. The oily formulation of claim 1, wherein propylene glycol monocaprylate, propylene glycol dicaprate and polyoxyethylene sorbitan monooleate represent a total amount of between 65 and 75% w/w of the oily formulation.

7. The oily formulation of claim 1, said oily formulation forming a self-microemulsion comprising droplets having a size of less than 200 nm when mixed with water or HCl.

8. A pharmaceutical composition comprising the oily formulation according to claim 1.

9. The composition of claim 8, which is in a form suitable for oral administration.

10. The composition of claim 9, wherein the form is a capsule.

11. The composition of claim 10, wherein the capsule is a soft gelatin capsule.

12. The composition of claim 11, said composition comprising between 100 and 400 mg mitotane.

13. The composition of claim 12, wherein the composition is a soft gelatin capsule encapsulating an oily formulation comprising a mitotane drug load between 33 to 66%; between 15 to 17% w/w propylene glycol monocaprylate; between 38 to 42% w/w propylene glycol dicaprate; and between 15 to 17% w/w polyoxyethylene sorbitan monooleate.

14. A method of treating a cancer, which method comprises administering a composition according to claim 1 to a patient in need of treatment.

15. A method for preparing a mitotane oily formulation suitable for forming a self-microemulsifying drug delivery system, comprising dissolving mitotane in a mixture of propylene glycol monocaprylate, propylene glycol dicaprate and polyoxyethylene sorbitan monooleate in proportions according to claim 1.

* * * * *

UNITED STATES PATENT AND TRADEMARK OFFICE
CERTIFICATE OF CORRECTION

PATENT NO. : 8,486,445 B2  
APPLICATION NO. : 13/322222  
DATED : July 16, 2013  
INVENTOR(S) : Florian Battung, Emad Hassan and Lionel Sansoe Page 1 of 1

It is certified that error appears in the above-identified patent and that said Letters Patent is hereby corrected as shown below:

In the Specification

Column 5,
Line 56, "Batch #054: 150" should read --Batch #054: 150%--.

Signed and Sealed this
Twenty-sixth Day of November, 2013

Margaret A. Focarino
*Commissioner for Patents of the United States Patent and Trademark Office*